United States Patent
El Kaffas (10) Patent No.: US 11,602,330 B2
(45) Date of Patent: Mar. 14, 2023

(54) MACHINE LEARNING TO EXTRACT QUANTITATIVE BIOMARKERS FROM RF SPECTRUMS

(71) Applicants: ONCOUSTICS INC., Toronto (CA); Ahmed El Kaffas, Palo Alto, CA (US)

(72) Inventor: Ahmed El Kaffas, Palo Alto, CA (US)

(73) Assignee: ONCOUSTICS INC., Toronto (CA)

( * ) Notice: Subject to any disclaimer, the term of this patent is extended or adjusted under 35 U.S.C. 154(b) by 275 days.

(21) Appl. No.: 16/772,304

(22) PCT Filed: Dec. 12, 2018

(86) PCT No.: PCT/US2018/065226
§ 371 (c)(1),
(2) Date: Jun. 12, 2020

(87) PCT Pub. No.: WO2019/118613
PCT Pub. Date: Jun. 20, 2019

(65) Prior Publication Data
US 2021/0077073 A1 Mar. 18, 2021

Related U.S. Application Data

(60) Provisional application No. 62/597,537, filed on Dec. 12, 2017.

(51) Int. Cl.
*A61B 8/00* (2006.01)
*A61B 8/08* (2006.01)
(Continued)

(52) U.S. Cl.
CPC ............ *A61B 8/5223* (2013.01); *A61B 8/463* (2013.01); *G06K 9/6223* (2013.01);
(Continued)

(58) Field of Classification Search
None
See application file for complete search history.

(56) References Cited

U.S. PATENT DOCUMENTS 6,238,342 B1 * 5/2001 Feleppa ............. A61B 17/3403
600/437
8,192,362 B2 * 6/2012 Kolios ..................... A61B 8/08
600/443
(Continued)

OTHER PUBLICATIONS

Uniyal et al., "Ultrasound RF Time Series for Classification of Breast Lesions," IEEE Transactions on Medical Imaging, vol. 34, No. 2, Feb. 2015 (Year: 2015).*

*Primary Examiner* — Soo Shin
(74) *Attorney, Agent, or Firm* — Nixon Peabody LLP (57) ABSTRACT

The present disclosure provides for ultrasound systems and methods to pre-process ultrasound data to distinguish abnormal tissue from normal tissue. An exemplary method can include receiving a set of ultrasound data and partitioning the set into a set of windows. The method can then provide for processing the set of windows to determine a power spectrum for each window. The power spectrum for each window can be processed to determine a normalized power spectrum for each window. This normalized power spectrum can be processed for each window with a machine learning model. The method can then provide for displaying an image where each window of the set of windows is displayed using a unique identifier based on the output of the machine learning model.

20 Claims, 6 Drawing Sheets

(51) Int. Cl.
  *G06K 9/62* (2022.01)
  *G06N 20/10* (2019.01)
  *G06N 3/04* (2006.01)
  *G06N 3/08* (2006.01)
  *G06T 7/00* (2017.01)
  *G06V 10/143* (2022.01)
  *G06V 10/22* (2022.01)
  *G06V 10/764* (2022.01)
  *G06V 10/82* (2022.01)
  *G16H 30/40* (2018.01)

(52) U.S. Cl.
  CPC ............. *G06K 9/6259* (2013.01); *G06N 3/04* (2013.01); *G06N 3/08* (2013.01); *G06T 7/0012* (2013.01); *G06V 10/22* (2022.01); *G16H 30/40* (2018.01); *G06T 2207/10132* (2013.01); *G06T 2207/20081* (2013.01); *G06T 2207/20084* (2013.01)

(56) References Cited

U.S. PATENT DOCUMENTS

| | | | | |
|---|---|---|---|---|
| 2016/0120502 A1* | 5/2016 | Sadeghi-Naini | ..... | A61B 8/5223 600/443 |
| 2016/0238568 A1* | 8/2016 | Feleppa | ................ | G16H 50/30 |
| 2017/0249739 A1* | 8/2017 | Kallenberg | .......... | G06V 10/454 |

* cited by examiner

MACHINE LEARNING TO EXTRACT QUANTITATIVE BIOMARKERS FROM RF SPECTRUMS

CROSS-REFERENCE TO RELATED APPLICATIONS

This application is the national phase of International Application No. PCT/US2018/065226, filed Dec. 12, 2018, which designated the U.S. and that International Application was published under PCT Article 21(2) in English. This application claims priority to and the benefit of U.S. Provisional Patent Application No. 62/597,537, filed Dec. 12, 2017, and entitled "Machine Learning to Extract Quantitative Biomarkers from Ultrasound RF Spectrums", the contents of which are herein incorporated by reference.

FIELD

The present invention is directed to ultrasound for classification and identification of various physiological aspects of a living organism, including tissue and biomarker identification and classification.

BACKGROUND

The following description includes information that may be useful in understanding the present invention. It is not an admission that any of the information provided herein is prior art or relevant to the presently claimed invention, or that any publication specifically or implicitly referenced is prior art.

Ultrasound imaging is widely used in clinical diagnosis and image-guided interventions. However, the field is relatively behind other areas of quantitative image analysis, including MRI, CT and X-ray analysis. For instance, many of the quantitative analysis techniques process the data from B-mode, after the ultrasound has already been converted into two dimensional images and much additional RF data has been removed. In other cases, the ultrasound RF data is analyzed using regression and best-fit models/analysis that yield specific known features for quantitative analysis. At times, these features can be directly correlated to specific tissue properties.

SUMMARY

The present disclosure provides for ultrasound systems and methods for detecting abnormal and normal tissue. An exemplary ultrasound system, according to a first embodiment of the present disclosure, can include a transducer, a memory, a signal processing unit, and one or more processors. The transducer can be configured to output a set of ultrasound data. The memory can contain machine-readable medium comprising machine-executable code having stored thereon instructions. The signal processing unit can include the one or more processors, where the one or more processors are coupled to the memory. The one or more processors can be configured to execute the machine executable code to cause the one or more processors to perform a series of steps. The series of steps can include receiving a set of ultrasound data and partitioning the set into a set of windows. The steps can then provide for processing the set of windows to determine a power spectrum for each window. The power spectrum for each window can be processed to determine a normalized power spectrum for each window. This normalized power spectrum can be processed for each window with a machine learning model. The steps can then provide for displaying an image where each window of the set of windows is displayed using a unique identifier based on the output of the machine learning model.

In some embodiments of the first disclosure, the machine learning model can be a k-means model or a model from a deep learning network. This can include (but is not limited to) one or a combination of the algorithm types of: a convolutional neural network (CNN), restricted Boltzmann machine (RBM), long short term memory (LSTM) or a capsule network (CapsNet).

In some examples, the machine learning model can be trained using ultrasound images labeled by a radiologist.

In some examples, the machine learning model can be an unsupervised model.

A second embodiment of the present disclosure can provide for a method of classifying tissue. The method can include first receiving a set of ultrasound data output from at least one ultrasound transducer. The set of ultrasound data output can represent a tissue of a patient. The method can then provide for partitioning the set of ultrasound data into a set of windows. The method can then provide for processing the set of windows with a machine learning model. The method can then provide for outputting a classification of the tissue.

In some examples, the classification can be a cancer status of the tissue.

In some examples, the method can further include processing the power spectrum for each window to determine a normalized power spectrum for each window in the set of windows.

In some examples the power spectrum can be taken using a continuous fast Fourier transform (FFT).

In some examples, the power spectrum can be taken using a discrete FFT.

A third embodiment of the present disclosure can provide for another method of classifying tissue. This method can provide for first receiving a set of ultrasound data output from at least one ultrasound transducer. The data can represent a tissue of a patient. The method can then provide for partitioning the set of ultrasound data into a set of windows. The method can then provide for processing the set of windows with a machine learning module. The method can then provide for outputting a classification of the tissue.

In some examples of the third embodiment, the step of processing the set of windows with a machine learning model can first include processing the set of windows to output a power spectrum for each window in the set of windows.

In some examples of the present disclosure, processing the set of windows with a machine learning model can first include processing the set of windows to output a time frequency domain processing technique.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION

Unless defined otherwise, technical and scientific terms used herein have the same meaning as commonly understood by one of ordinary skill in the art to which this invention belongs. Szycher's Dictionary of Medical Devices CRC Press, 1995, may provide useful guidance to many of the terms and phrases used herein. One skilled in the art will recognize many methods and materials similar or equivalent to those described herein, which could be used in the practice of the present invention. Indeed, the present invention is in no way limited to the methods and materials specifically described.

In some embodiments, properties such as dimensions, shapes, relative positions, and so forth, used to describe and claim certain embodiments of the invention are to be understood as being modified by the term "about."

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Overview

Conventional ultrasound spectroscopy uses ultrasound frequency spectrums from ultrasound RF data (raw sound signal as it returns into transducer) to extract specific, pre-defined quantitative parameters that can describe tissue state (e.g., information on the ultrasound scatter size, concentration and change in impedance in tissue).

In some conventional applications, systems extract sets of parameters to characterize and classify tissue from RF, or a frequency-domain RF (employing a Fourier or wavelet transform). This process takes the RF data and first normalizes it to a calibration spectrum (acquired separately) to remove the machine setting, some artifacts and some user dependencies. Next, it extracts parameters, which are correlated to different tissue pathologies. This is done by taking a certain segment of the spectrum (with an established bandwidth around the center frequency of the signal) and fitting it to a specific mathematical model or simple linear regression. However, the parameters and quality of fit are not ideal, and predetermined models and parameters usually miss valuable information degrading the accuracy and specificity of classification using these methods.

Ultrasound RF data, both beam-formed and pre-beam-forming, contains more information than standard, B-mode or 2-D, ultrasound images as collected according to the conventional methods described above. Though useful, B-mode images, which are perceptible and interpretable by human vision, require discarding the majority of ultrasound RF data to create them. The present disclosure provides for extracting, processing, and categorizing this normally-discarded information from the ultrasound RF data. This normally-discarded information can be analyzed using computer algorithms, such as ML or deep learning methods, to recover and reveal signal information that is beyond human perception. This is unexpected and surprising, since state-of-the-art applications of artificial intelligence (AI) only enhance recognition and awareness (for example, of photographs or language) within the bounds of human senses, cognizance and comprehension.

The present disclosure therefore uses machine learning to take ultrasound images and to train machine learning models to recognize certain pathologies based on these conventionally qualitative images. Effectively, this system is used to automate the clinical process of a clinician analyzing images from the processed ultrasound data. However, conventional clinical images (e.g. two dimensional B-mode images) are heavily processed from the raw ultrasound data and though they appear good qualitatively, they lack information about tissue microstructure.

However, it has been discovered that using artificial intelligence/machine learning methods ("ML") to analyze the ultrasound data as is—instead of conventional mathematical models or "fits" that parameterize the signal—provides for vastly increased accuracy and specificity. Particularly, this allows for more accurate and specific classification and identification of tissue types and biomarkers related to tissue—including for disease states. Additionally, it has been discovered that applying the ML models to the raw data or the frequency spectrum data—rather than the images (e.g. B-mode) after processing—provides much more accurate results because the already heavily processed images have much of the important ultrasound data filtered out, including that which is useful for diagnosis and classification (e.g., a lot of the microstructure of tissue is lost when processing the data to form images).

In some examples, the entire spectrum of data or a specific subset of the spectrum can be used as a feature set to train an ML model to evaluate and classify tissues in ultrasound images for screening, diagnostics and treatment monitoring applications. The spectrum-based features as is, or normalized (using standard methods) can be used as is, or combined with conventional parameters from linear regression or mathematical models. The RF ultrasound data may be converted to a normalized power spectrum which may then be fed into a trained (supervised, unsupervised or deep learning method) ML model(s) to classify tissues for specific applications, or to find specific multi-parametric biomarkers, or to identify and apply previously unknown parameters of normal and pathological physiology. In other examples, the raw data before conversion to spectra, or the RF converted to other domains (i.e. Laplace transform, principal component analysis, etc.) may be input to ML learning algorithms.

Ultrasound System

Figure 1:
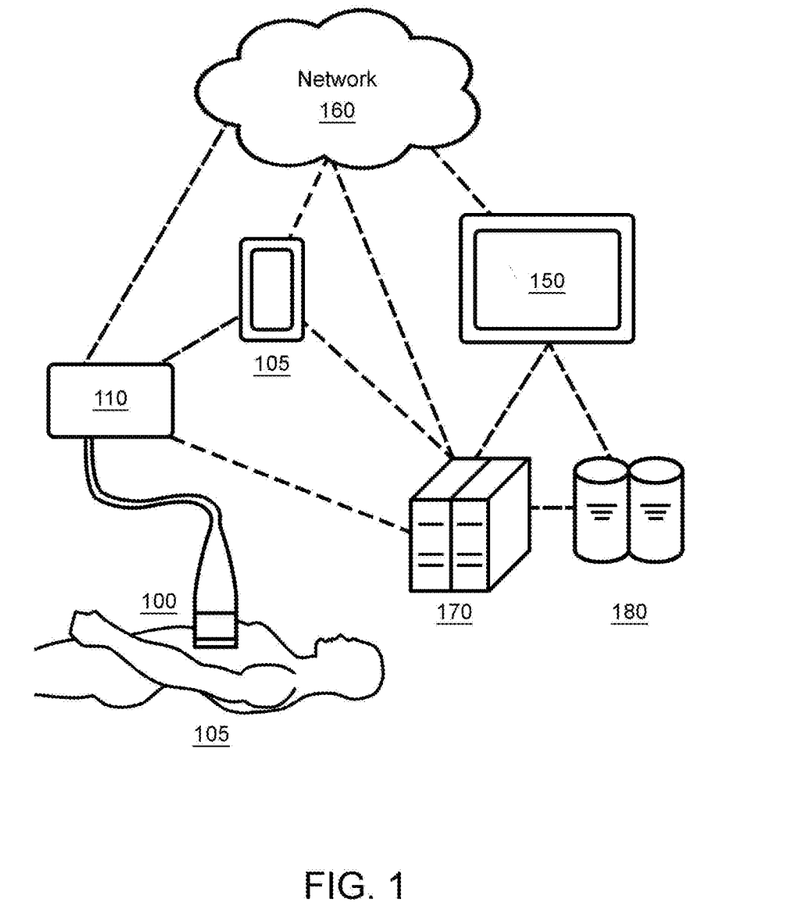
FIG. 1 depicts a perspective view of an overview of an ultrasound system.

Various conventional ultrasound systems may be utilized that include an ultrasound transducer and signal processing equipment. For instance, FIG. 1 illustrates an example of an ultrasound system that includes an ultrasound transducer 100, a signal processor 110, a mobile device 105, a network 160, display 150, server 170, and database 180.

In this example, a handheld ultrasound transducer 100 contained in a handheld case (e.g. ultrasound probe) is utilized. In other examples, a robotic arm transducer or other transducer 100 implementations may be utilized. In some examples, to focus the ultrasound beam, the transducer 100 may use phased array techniques, shaping of the transducer 100 or utilize a physical lens.

In some examples, materials on the face of the transducer 100 enable the sound to be transmitted efficiently to the patient's body 105 (e.g. human, animal) by impedance matching. For instance, this may be a rubber or other coating. In addition, a water based gel may be utilized between the patient's skin and the ultrasound transducer case. The sound waves propagate through the patient 105 until they are reflected in places where the acoustic impedance changes in the patient's 105 body. The return of the sound wave is then detected by the transducer(s) 100, which is converted to a signal that is the RF data. The RF data can be pre-beamforming in or post-beamforming.

The ultrasound data output from the transducer 100 may be processed by a processing unit 110 or other associated processors and computing devices in various ways as disclosed herein. In some cases, after processing an image showing various identified tissues or other indicators may be displayed on a display 150. The ultrasound data may be processed fully or partially by electronics included within the transducer 100 casing, on a separate processing unit 110, or an electrically connected computing device. In other examples, the data can be fully or partially processed on a local or remote server 170 connected to the processing unit 110 and/or transducer through a network 160.

Processing and display of the ultrasound data may also take place fully or partially on an associated mobile device 105, or results of the processing may be sent to and displayed on a mobile device 105. An associated database 180 may store the ultrasound data, models utilized for processing the data, and information about various patients and testing 105. Additionally, a server 170 or separate servers 170 may process training data to form and/or update the models and store them on a database 180.

The system may connect to a variety of different ultrasound transducers 100 and/or signal processing units 110. This data maybe aggregated and analyzed by a server(s) 170 and may be stored on databases 180. The data from different processing units 110 could be utilized to continually update and train a model for processing the data, based on different types of patients and ultrasound units (e.g., for different types of transducers 100). Accordingly, the RF signal can be at any stage before image formation pre-beamforming, pre-scan conversion, post beamforming, post-scan conversion, etc.

Ultrasound Data Processing Methods

Figure 2:
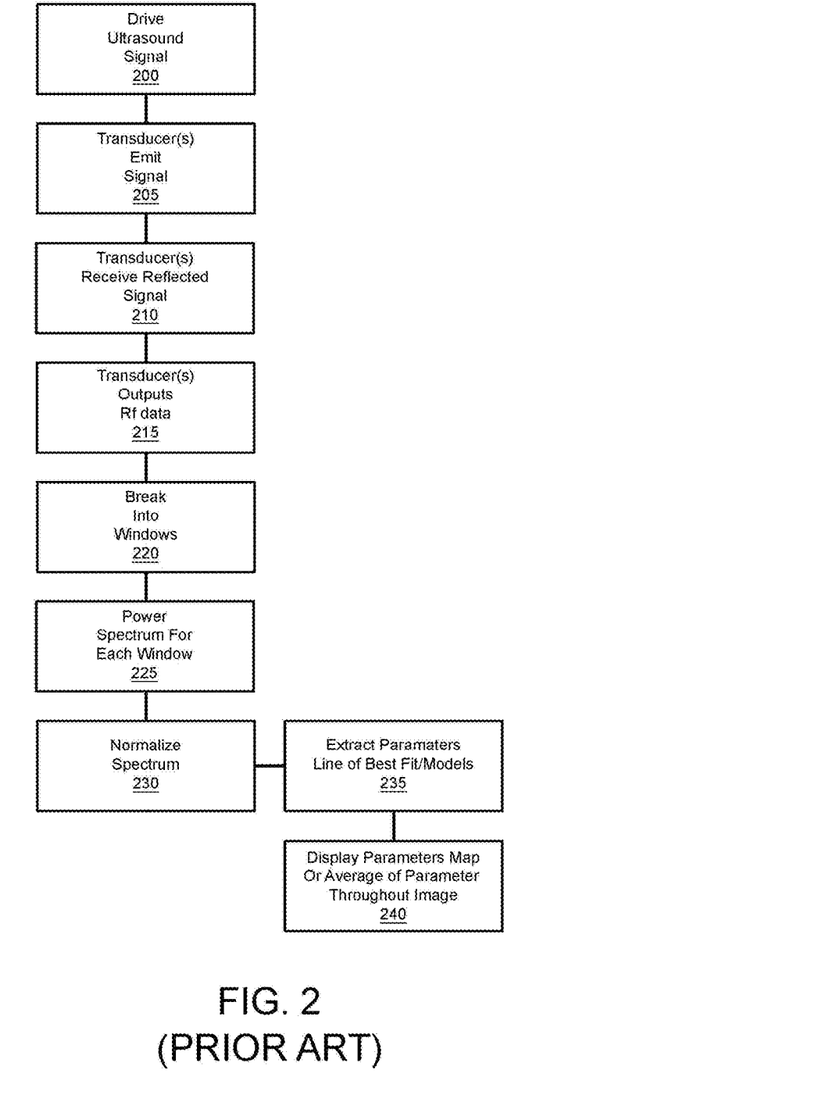
FIG. 2 depicts a flowchart showing a prior art method of tissue classification.

Previously described ultrasound processing methods are illustrated in the flowchart of FIG. 2. For instance, most ultrasound systems include a driver that drives the ultrasound signal 200 sent to the transducer 100. Then, the transducer 100 vibrates and emits the ultrasound signals 205 that are directed toward a patient's 105 body. The transducer then detects the reflected signals 210, and outputs the ultrasound data or raw RF data 215. Then, in previously described systems, the raw ultrasound data is typically broken up into various windows 220. Then, the power spectral for each window 225 may be determined, and the spectrum normalized 230 to calibrate for certain hardware and parameters settings (to be independent to system and acquisition parameters properties). Then, the parameters maybe extracted 235 using line of best fit or other regression models. The system them would display a parametric map or average of the parameters throughout the image 240.

Figure 3:
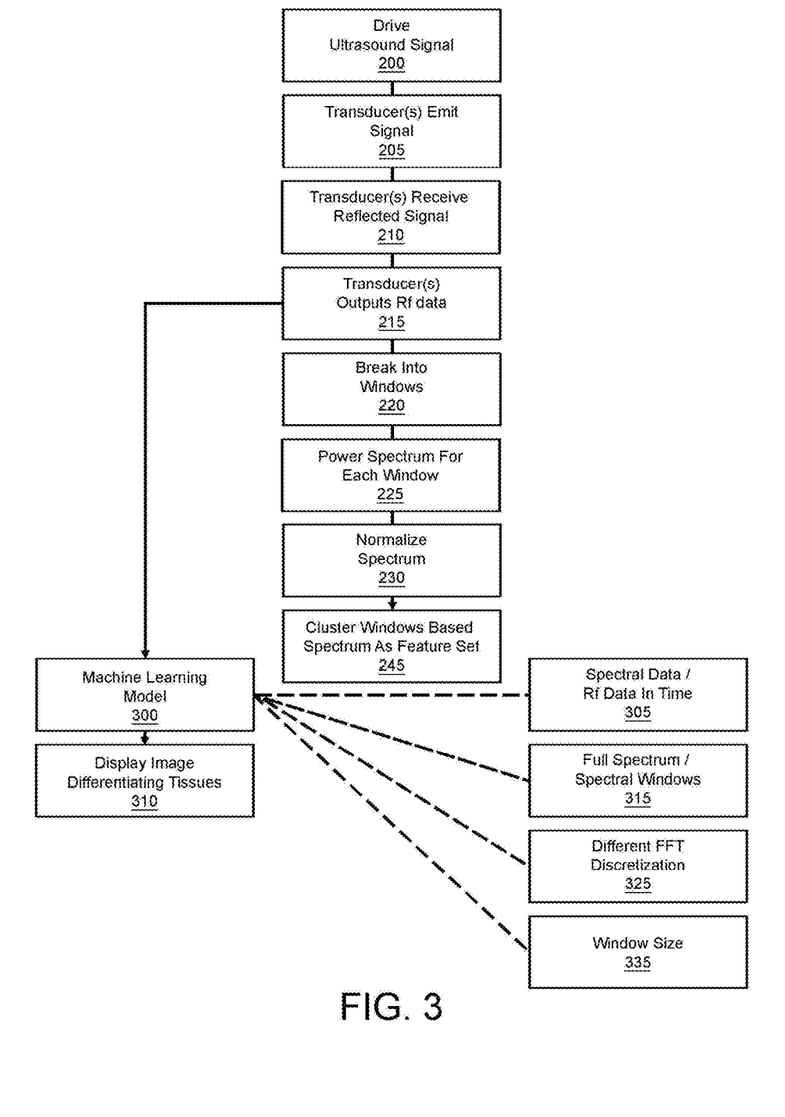
FIG. 3 depicts an example of a flowchart showing a method for classification of tissue using machine learning analysis of ultrasound data.

FIG. 3 illustrates an example of an ultrasound processing method according to the present disclosure. As illustrated, the steps through outputting of the raw ultrasound data from the transducer 215 are largely the same. However, as illustrated, once the raw ultrasound data is output from the transducer 100, the processing steps may follow a similar or different path, but then are ultimately processed by a machine learning model 300.

In some examples, the same steps of breaking the data into windows 220, performing a power spectrum for each window 225, and normalizing the spectrum 230 may be the same. For instance, many applications use a Fourier transform to turn the raw ultrasound data into spectral data for further analysis. In other examples, the raw ultrasound data may be input directly into a machine learning model 300, or optionally may undergo initial filtering techniques and transformations other than frequency processing and then may be fit into a machine learning model 300 without first converting the data into the frequency domain.

In some examples, the normalized power spectrums output for each window 225 may be used as a feature set 245 input into a machine learning model (step 300). Window size can be adjusted in step 335. The spectrum is typically discretized to be representative of the continuous spectrum to obtain the set of features. In some examples, a set of windows of data can be processed to output a time frequency domain processing time (step 305). In some examples, different processing techniques may utilize non-normalized or normalized spectrums, full spectrum or windows of spectrums 315, or in other examples the raw RF data may be input into the machine learning model or any other form of processed RF data. In some examples, different Fourier transform discretization 325 may be utilized to develop features.

In these examples, the machine learning model 300 utilized may be a model trained to find a specific type of tissue. For instance, a server 170 may constantly process new data to update and train the model to recognize, for instance, liver cancer based on a signature the model recognizes. The model may be different kinds of neural networks, deep learning neural networks, supervised or unsupervised models, or other suitable types of machine learning models.

Therefore, the present disclosure does not rely on applying artificial intelligence, machine learning, or deep learning to images made with ultrasonography (e.g. B-mode) or rely on performing quantitative ultrasound spectroscopy (QUS). Rather, the present disclosure provides for pre-processing techniques from ultrasound spectroscopy and then feeding the power spectrum signal into a trained AI, ML or deep learning model. Feeding the power spectrum signal as such is a new step provided for by the present disclosure, which can avoid parameterization and normalize the data. Other feature sets, beyond the normalized power spectrum (NPS), can be used to train and supplement the NPS being fed into the models of the present invention. Therefore, the present disclosure provides for generating clean data and eliminating several sources of signal error (including system-specific sources of variability) by pre-processing the data. This approach additionally allows for improved training on high quality data normalized to a spectrum, and has the potential to reduce the data set size needed for training. In some embodiments of the present disclosure, training can also be performed on channel data.

RF data is the foundation to all ultrasound systems, and the methods disclosed herein allow calibration of signals originating from different systems. The present disclosure demonstrates an application of knowledge transfer. Systems and methods according to the present disclosure can separate abnormal tissue from normal tissue. This form of tissue characterization enables classification and diagnostics. The systems and methods of the present disclosure can be applied on low-cost, point-of-care (POC) ultrasound systems, which have limited function and are not usually used for diagnostic tissue characterization. The present disclosure thus enables POC devices to perform new diagnostic applications. With the right labeling information for training, the present disclosure thus provides for detecting and yielding tissue pathologies from ultrasound RF signal data that are beyond human ability to decipher. Conventional, current image formation methods, and applied algorithms, by contrast to the methods of the present disclosure, remain constrained to enhancing what a radiologist can see.

EXAMPLES

The following examples are provided to better illustrate the claimed invention and are not intended to be interpreted as limiting the scope of the invention. To the extent that specific materials or steps are mentioned, it is merely for purposes of illustration and is not intended to limit the invention. One skilled in the art may develop equivalent means or reactants without the exercise of inventive capacity and without departing from the scope of the invention.

Several different modes of ultrasound are known. For instance, in A-mode (amplitude mode), a single transducer scans a line through the body with echoes plotted on screen as a function of depth. B-mode or 2D mode uses a linear array of transducers to simultaneously scan a plane through the body that case be viewed as a two dimensional image on screen.

Figure 5:
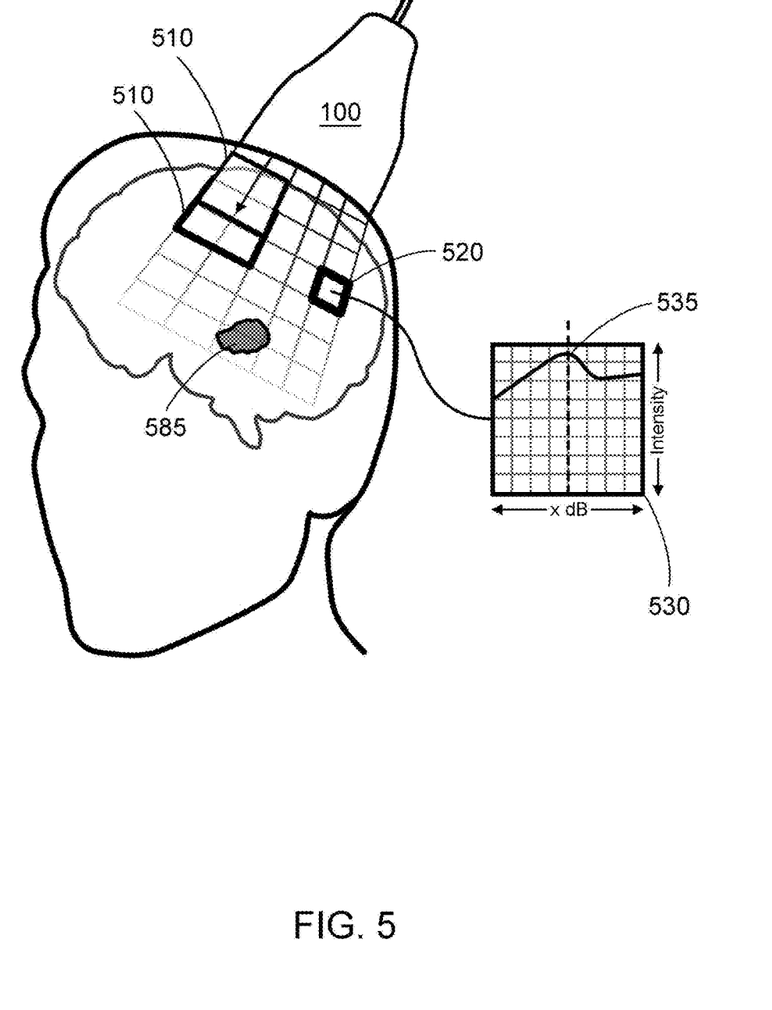
FIG. 5 depicts a schematic diagram of an ultrasound image analysis system.

FIG. 5 illustrates an example of an ultrasound transducer 100 aimed at a patient's body, that would penetrate into the body and potentially identify an abnormal, diseased, or other types of tissue 585 in the liver for example. For instance, the transducer 100 may contain a linear array of transducers 100 as illustrated in FIG. 5. Each of the transducers 100 would emit or vibrate at a certain frequency (or multiple frequencies) and sound waves would enter the patient's body. For instance, the ultrasound transducers 100 may emit sound pulses with a Gaussian intensity curve (intensity v frequency) around a central frequency within the range of, for example, 1-5 megahertz. For instance, the transducer(s) 100 may emit an acoustic wave that it is centered around 2 megahertz, and includes frequencies around 2 megahertz with decreasing intensity to form a Gaussian curve around 2 megahertz.

When the emitted sound waves encounter various structures of the body that have different acoustic properties, portions of the sound waves get reflected back to the transducer 100 at the boundary between the structures. The greater the difference in the acoustic properties, the greater is the intensity or energy of the reflected waves. Additionally, structures of the body contribute to attenuation of the signal and scattering.

Then, once the reflected sound waves hit one or more transducer(s) the transducers will record the exact time of flight when the received wave is registered. Additionally, the intensity of the wave or pulse will be determined. Using the time of flight and the linear array of transducers 100, the system can reconstruct a two dimensional grid or data segments of ultrasound RF data that includes an array of frequencies, intensities and other data at each data segments 520. Generally, the array of frequencies can be converted into a power spectrum curve 530 that shows the returned intensity of the acoustic signal at various of frequencies. In some examples, the system will only record different sized bands of frequencies around the emission frequency or a frequency near the emission frequency. In some examples, the bands may be 4, 5, 6, 7, or 8 dB wide.

In the case of a linear array of transducers, the system may use beamforming or other techniques that utilize concepts of destructive and constructive interference to reconstruct the frequencies and intensities for each data segments of an ultrasound plane along each RF line. As discussed earlier, in some examples, the signals may be processed into a two dimensional array of data segments that represent different readings or data at each data segment, and in turn each represent the reflected ultrasound signal at a certain location in the object (e.g., a portion of the liver if the transducer 100 is aimed at a patient's body).

In some examples, a reference will then be applied to each of the data segments 520 to normalize a reference tissue to the curve obtained from the object or patient. In other examples, the raw data output from the transducers will be processed by a machine learning model 300 to allow it to find the features. In some examples, a power spectrum 535 will be taken of each data segment 520. In some examples a larger window 510 or sliding window 510 or a bounding box 510 (as in a YOLO, "You Only Look Once," strategy) or anchor box 510 may be applied to a matrix of data segments to average or combine using other statistical techniques to provide a power spectrum 535 or other data set for each window 510.

Then, a machine learning algorithm 300 may be applied to the data set for each data segment 520, or each window 510. This may be used to classify the tissue represented in the window 510 or data segments 520. For instance, the system may classify the tissue in the window 510 as abnormal, cancerous, water, bone, or air. In some examples, the system may utilize the input of all of the data segments 520 or windows 510 to then classify each tissue, or classify larger portions of the tissue, such as a region of interest.

Then, once each data segment 520 or window 510 is classified, the system may display an image differentiating the tissues 310 by classification. The image could be displayed as a heatmap or other map similar to FIG. 4A, or could have numeric values, diagnosis, or other classification mapped to each section of tissue. In some examples, the system may output whether or not the tissue contains any cancerous cells after classifying each of the data segments 520 or windows 510.

Figure 4A:
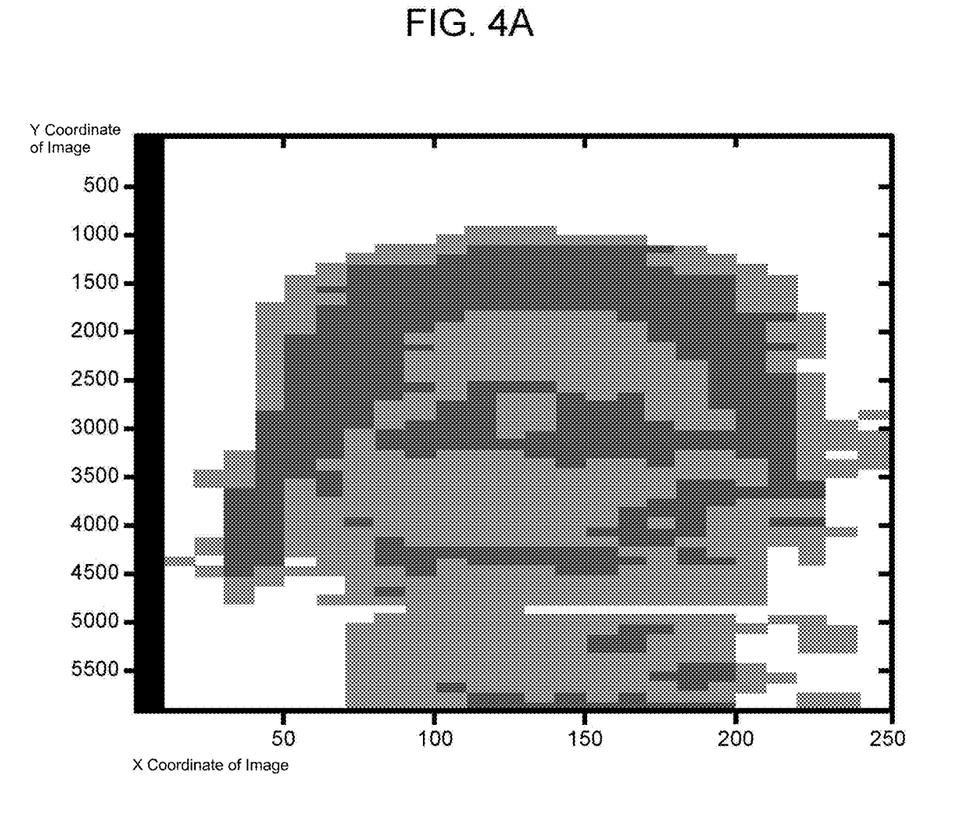
FIG. 4A depicts an example image of a mouse tumor using the systems and methods disclosed herein to segment the image using k-means clustering.
Figure 4B:
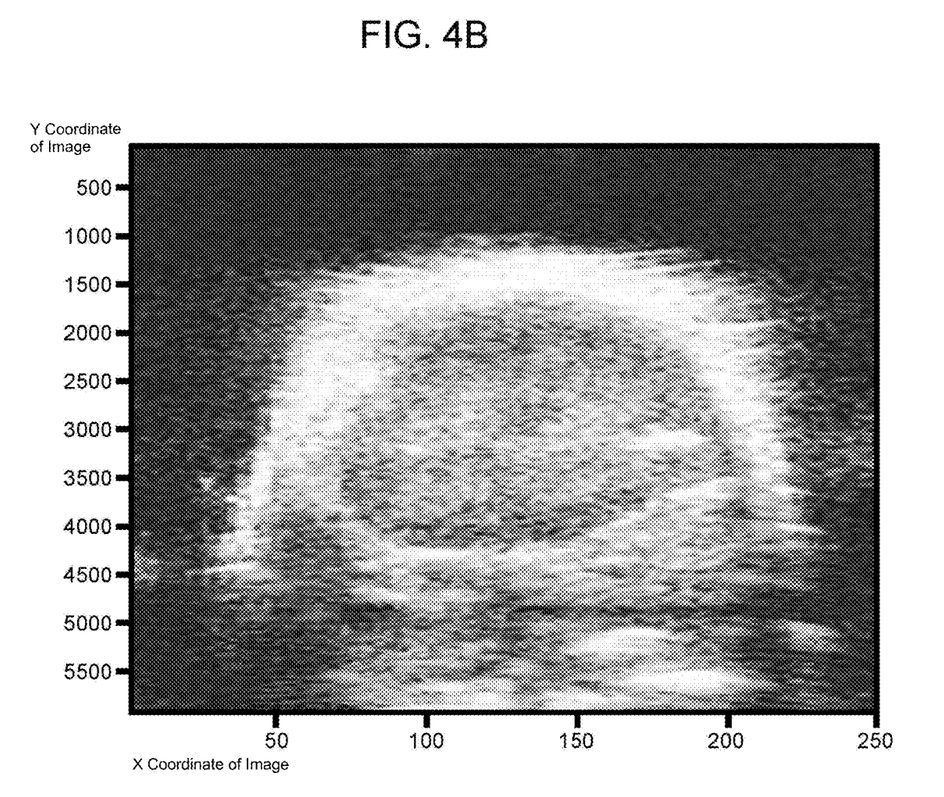
FIG. 4B depicts the original ultrasound image that was processed for FIG. 4A.

By contrast to FIG. 4A, FIG. 4B shows the original ultrasound image that was processed according to a method of the present disclosure to yield FIG. 4A. The contrast between FIGS. 4A and 4B shows the effectiveness of the present disclosure at producing data which can be readily analyzed and classified.

Machine Learning Models

In some examples, the machine learning model 300 will be an unsupervised algorithm. In other examples, the machine learning model 300 will be supervised. The, machine learning model 300 may take a variety of forms. For instance, the system may utilize more basic machine learning tools including 1) decision trees ("DT"), (2) Bayesian networks ("BN"), (3) artificial neural network ("ANN"), or (4) support vector machines ("SVM"). In other examples, deep learning algorithms or other more sophisticated machine learning algorithms, e.g., convolutional neural networks ("CNN"), or capsule networks ("CapsNet") may be used.

DT programs are generally used because of their simplicity and ease of understanding. DT are classification graphs that match input data to questions asked at each consecutive step in a decision tree. The DT program moves down the "branches" of the tree based on the answers to the questions (e.g., First branch: Is the patient male? yes or no. Branch two: Is the patient having trouble urinating? yes or no, etc.).

Bayesian networks ("BN") are based on likelihood something is true based on given independent variables and are modeled based on probabilistic relationships. BN are based purely on probabilistic relationships that determine the likelihood of one variable based on another or others. For example, BN can model the relationships between symptoms and diseases. Particularly, if a patient's symptoms or biomarkers levels are known, a BN can be used to compute the probability that a patient has a particular disease. Thus, using an efficient BN algorithm, an inference can be made based on the input data. They are commonly used by the medical domain to represent reasoning under uncertain conditions for a wide range of applications, including disease diagnostics, genetic counseling, and emergency medical decision support system (MDSS) design.

Artificial neural networks ("ANN") are computational models inspired by an animal's central nervous system. They map inputs to outputs through a network of nodes. However, unlike BN, in ANN the nodes do not necessarily represent any actual variable. Accordingly, ANN may have a hidden layer of nodes that are not represented by a known variable to an observer.

ANNs are capable of pattern recognition and have been used for the medical and diagnostics fields. Their computing methods make it easier to understand a complex and unclear process that might go on during diagnosis of an illness based on input data a variety of input data including symptoms. While still facing steep limitations, ANN has demonstrated to be suitable in a clinical decision support system design and other biomedical applications, such as diagnosis of myocardial infarction, MDSS for leukemia management, and cancer detection.

Support vector machines ("SVM") came about from a framework utilizing of machine learning statistics and vector spaces (linear algebra concept that signifies the number of dimensions in linear space) equipped with some kind of limit-related structure. In some cases, they may determine a new coordinate system that easily separates inputs into two classifications. For example, a SVM could identify a line that separates two sets of points originating from different classifications of events.

They have been applied practically and are theoretically well-founded, but can sometimes be difficult to understand. SVMs have been applied to a number of biological domains, such as MDSS for the diagnosis of tuberculosis infection, tumor classification, and biomarker discovery.

However, there is a relatively new type of machine learning algorithm that is capable of modeling very complex relationships that have a lot of variation that are called deep neural networks. Deep neural networks (DNN) have developed recently to tackle the problems of speech recognition.

In the IT industry fields, various architectures of DNN have been proposed to tackle the problems associated with algorithms such as ANN by many researchers during the last few decades. These types of DNN are CNN (Convolutional Neural Network), RBM (Restricted Boltzmann Machine), LSTM (Long Short Term Memory) etc. They are all based on the theory of ANN. They demonstrate a better performance by overcoming the back-propagation error diminishing problem associated with ANN.

In some examples, clustering based on k-means, or K-nearest neighbors approaches may be a useful machine learning model 300. In other examples, a K-means clustering methods may be used as machine learning models 300. In other examples, principle component analysis can be utilized to separate the data and classify the tissues.

Machine Learning—Training Data

Machine learning models 300 require training data to identify the features of interest that they are designed to detect. For instance, various methods may be utilized to form the machine learning models 300 including applying randomly assigned initial weights for the network and applying gradient descent using back propagation for deep learning algorithms. In other examples, a neural network with one or two hidden layers can be used without training using this technique.

In some examples, the machine learning models 300 will be trained using labeled data, or data that represents certain features, specific tissues, diagnosis, or stage of diagnosis of tissues. In other examples, the data will only be labeled with the outcome and the various relevant data may be input to train the machine learning algorithm.

For instance, to classify a tissue or window of tissue, various machine learning models 300 may be utilized that input various data disclosed herein. In some examples, the input data will be labeled by correlating by having a certified radiologist label the tissues, windows 510 or data segments 520 that include cancer data. Accordingly, the input to the machine learning algorithm for training data may be cancer boxes or non-cancerous. In other examples, it may include additional labels including water, tissue, bone, and air.

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessarily represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. An ultrasound system comprising:
a transducer configured to output a single static set of raw ultrasound radio frequency (RF) data forming a single frame of a tissue area;
a memory containing machine readable medium comprising machine executable code having stored thereon instructions;
a signal processing unit comprising one or more processors coupled to the memory, the one or more processors configured to execute the machine executable code to the cause the one or more processors to:
receive the single static set of raw ultrasound RF data;
process the single static set of raw RF ultrasound data with a machine learning model; and
output classification of the raw RF ultrasound data from an output of the machine learning model.

2. The ultrasound system of claim 1, wherein the machine learning model is a k-means model or a model from a deep learning network comprising but not limited to one or a combination to the algorithm types of CNN (Convolutional Neural Network), RBM (Restricted Boltzmann Machine), LSTM (Long Short Term Memory) or CapsNet (Capsule Networks).

3. The ultrasound system of claim 1, wherein the machine learning model is trained using ultrasound images labeled by a radiologist.

4. The ultrasound system of claim 1, wherein the machine learning model is an unsupervised model.

5. The system of claim 1, wherein the processor is operable to display an image representing the set of ultrasound data using a unique identifier based on the output of the machine learning model.

6. A method comprising:
receiving a single static set of raw ultrasound radio frequency (RF) data output from at least one ultrasound transducer, the single static set of raw ultrasound RF data forming a single frame representing a tissue area of a patient;
processing the single static set of raw ultrasound RF data set of windows to determine a power spectrum;
processing the determined power spectrum as an input into a machine learning model; and
outputting a classification of the tissue area from the machine learning model.

7. The method of claim 6, wherein the classification is a cancer status of the tissue.

8. The method of claim 6, wherein the method further comprises processing the power spectrum to determine a normalized power spectrum.

9. The method of claim 6, wherein the power spectrum is taken using a continuous Fast Fourier Transform (FFT).

10. The method of claim 6, wherein the power spectrum is taken using a discrete FFT.

11. A method comprising:
receiving a single static set of raw ultrasound radio frequency (RF) data output from at least one ultrasound transducer forming a single frame representing a tissue area of a patient;
processing the single static set of ultrasound RF data as an input to a machine learning model; and
outputting a classification of the tissue area from the machine learning model.

12. The method of claim 11 further comprising:
partitioning the single static set of raw ultrasound RF data into a set of windows or bounding boxes; and
processing the set of windows to output a power spectrum for each window of the set of windows.

13. The method of claim 12, wherein the step of processing the set of windows comprises processing the set of windows to output a time frequency domain processing technique.

14. The method of claim 11, wherein the machine learning model is a k-means model or a model from a deep learning network comprising one or a combination to the algorithm types of CNN (Convolutional Neural Network), RBM (Restricted Boltzmann Machine), LSTM (Long Short Term Memory) or CapsNet (Capsule Networks).

15. The method of claim 11, wherein the machine learning model is trained using ultrasound images labeled by a radiologist.

16. The method of claim 11, wherein the machine learning model is an unsupervised model.

17. The method of claim 11, wherein the classification is a cancer status of the tissue.

18. The method of claim 11, further comprising outputting a specific multi-parametric biomarker from the machine learning model.

19. An ultrasound system comprising:
a transducer configured to output a single static set of raw ultrasound radio frequency (RF) data forming a single frame of a tissue area; and
a signal processing unit operable to:
receive the single static set of raw ultrasound RF data
process the set of single static set of raw ultrasound RF data to determine a raw power spectrum;
process the raw power spectrum as an input to a machine learning model; and
output a classification of the raw power from an output of the machine learning model.

20. The system of claim 19, further comprising a display, wherein the signal processing unit is operable to display an image representing the set of power spectrum data using a unique identifier based on the output of the machine learning model on the display.

* * * * *